(12) United States Patent
Northen et al.

(10) Patent No.: US 10,822,634 B2
(45) Date of Patent: Nov. 3, 2020

(54) DETERMINATION OF LIGNINASES ACTIVITIES BY NANO-STRUCTURE INITIATOR MASS SPECTROMETRY

(71) Applicants: The Regents of the University of California, Oakland, CA (US); National Technology & Engineering Solutions of Sandia, LLC, Albuquerque, NM (US)

(72) Inventors: Trent R. Northen, Walnut Creek, CA (US); Kai Deng, Orinda, CA (US)

(73) Assignees: The Regents of the University of California, Oakland, CA (US); National Technology & Engineering Solutions of Sandia, LLC, Albuquerque, NM (US)

( * ) Notice: Subject to any disclaimer, the term of this patent is extended or adjusted under 35 U.S.C. 154(b) by 489 days.

(21) Appl. No.: 15/499,769

(22) Filed: Apr. 27, 2017

(65) Prior Publication Data

US 2017/0314058 A1   Nov. 2, 2017

Related U.S. Application Data

(60) Provisional application No. 62/328,603, filed on Apr. 27, 2016, provisional application No. 62/475,138, filed on Mar. 22, 2017.

(51) Int. Cl.
| | | |
|---|---|---|
| *C12Q 1/26* | (2006.01) | |
| *C12Q 1/28* | (2006.01) | |
| *C12Q 1/34* | (2006.01) | |
| *G01N 33/68* | (2006.01) | |

(52) U.S. Cl.
CPC .............. *C12Q 1/26* (2013.01); *C12Q 1/28* (2013.01); *C12Q 1/34* (2013.01); *C12Y 110/03002* (2013.01); *G01N 33/6848* (2013.01); *G01N 2333/908* (2013.01); *G01N 2333/90232* (2013.01); *G01N 2333/924* (2013.01); *G01N 2560/00* (2013.01)

(58) Field of Classification Search
CPC ........................................................ C12Q 1/26
USPC .............................................................. 702/12
See application file for complete search history.

(56) References Cited

U.S. PATENT DOCUMENTS

| | | |
|---|---|---|
| 9,082,600 B1 | 7/2015 | Greving |
| 9,125,596 B2 | 9/2015 | Leclerc et al. |
| 9,460,904 B1 | 10/2016 | Greving |
| 2008/0128608 A1 | 6/2008 | Northen et al. |
| 2012/0225797 A1 | 9/2012 | Northen et al. |
| 2014/0247115 A1 | 9/2014 | Leclerc et al. |
| 2014/0329274 A1 | 11/2014 | Bowen et al. |
| 2015/0330992 A1 | 11/2015 | Northen et al. |

FOREIGN PATENT DOCUMENTS

| | | |
|---|---|---|
| WO | WO/2013/036885 A1 | 3/2013 |
| WO | WO/2017/062481 A1 | 4/2017 |

OTHER PUBLICATIONS

Northern et al. "A Nanostructure-Initiator Mass Spectrometry-Based Enzyme Activity Assay" PNAS (2008) vol. 105, No. 10, pp. 3678-3683 (Year: 2008).*
Northen et al, Clathrate Nanostructures for Mass Spectrometry, Nature (2007), 449 (7165): 1033-6.
Northen et al, A nanostructure-initiator mass spectrometry-based enzyme activity assay. PNAS (2008) 105, 3678-3683.
Woo et al, Nanostructure-initiator mass spectrometry: a protocol for preparing and applying NIMS surfaces for high-sensitivity mass analysis. Nature Protocols (2008) vol. 3 No. 8,1341.
Kawai et al. Simple method for synthesizing phenolic 11-0-4 dilignols. J.Wood Sci (1999) 45: 440-443.
Wu et al. Hydrogenolysis of 13-04 lignin model dimers by a ruthenium-xantphos catalyst. Dalton Transactions (2012) 41, 11093.
Reindl et al. Colloid-based multiplexed screening for plant biomass-degrading glycoside hydrolase activities in microbial communities. Energy Envron. Sci. (2011) 4, 2884.
Deng et al. Rapid characterization of the activities of lignin-modifying enzymes based on nanostructure-initiator mass spectrometry (NIMS). Biotechnol Biofuels (2018) 11: 266.

\* cited by examiner

*Primary Examiner* — Jerry Lin
(74) *Attorney, Agent, or Firm* — Robin C. Chiang; Lawrence Berkeley National Laboratory

(57) ABSTRACT

A method for rapid, high throughput screening of the activities of enzymes, especially ligninases and its enzyme cocktails, using nanostructure initiator mass spectrometry (NIMS) surfaces, substrates and methodology.

23 Claims, 17 Drawing Sheets

Compound 2a      Compound 2b

Compound 3a      Compound 3b

Compound 3c

1) Phenolic beta-aryl ether dimer NIMS substrates

2) Nonphenolic beta-aryl ether dimer NIMS substrate

Amide bond formation

TSTU m.w. 940

TFP ester:
Probe for the primary amine

Capture of lysine with TFP ester:

Product m.w. 920

DETERMINATION OF LIGNINASES ACTIVITIES BY NANO-STRUCTURE INITIATOR MASS SPECTROMETRY

RELATED PATENT APPLICATIONS

The application claims priority to U.S. Provisional Patent Application Ser. Nos. 62/328,603, filed Apr. 27, 2016, and 62/475,138, filed Mar. 22, 2017, both of which are herein incorporated by reference in their entireties.

This application is related to U.S. Patent Pub. No. 2012/0225797, co-pending U.S. patent application Ser. No. 14/651,546 filed on Jun. 11, 2015, and U.S. patent application Ser. No. 13/363,695 filed on Feb. 1, 2016, all of which are hereby incorporated by reference in their entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention relates to assays for determining enzyme activity, specifically ligninases, using mass spectrometry.

BACKGROUND OF THE INVENTION

Lignin is the third major components of lignocellulosic biomass and has the potential as valuable starting materials for the production of biofuels or biomaterials. The proper deconstruction of lignin will significantly add the value to the overall utilization of lignocellulosic biomass. The efficiency of the breakdown of lignin is closely connected to the availability of optimal ligninases, which are enzymes that are responsible for breaking down lignin into simpler aromatics. In order to find the high performance ligninases and ligninases cocktails, a high throughput screening method is needed. Currently, there is no such high throughput method available.

Currently, GC_MS and/or LC_MS are the predominant methods that people use to quantify the products from ligninase degradation of dimer model compounds. However, they are low throughput and sometimes overlapping peaks make quantitation difficult.

SUMMARY OF THE INVENTION

In one embodiment, the invention provides for the development of a novel assay to study ligninase activities. Model substrates are designed and synthesized to contain the common lignin linkages, a fluorous tails and an ionization helper. Different mass tags can be attached to different model substrates. All substrates (substrates for ligninases, cellulases, hemicellulases etc.) are mixed together to realize multiplexing assays for simultaneously detection of multiple enzyme activities in high-throughput manner. This cannot be done with any previous method.

In a typical assay, our model substrates were treated with ligninases of interest. Certain bonds are being cleaved or formed based on different ligninase activities and result in the loss or addition of molecular weight of model compounds. Then the products were analyzed by nanostructure initiator mass spectrometry. It is a novel, surfaced based desorption ionization techniques. The biggest advantages of this assay is that due to the special surface, only our substrates and products can stick onto the teflon like surface, all other impurities, like proteins, salts, and the like, can be washed away. This process can significantly increase the signal to noise ratio to facilitate the analysis.

Our assays are perfectly fit with the high throughput platform that we have built for screening cellulase and hemicellulase activities. Large numbers of enzymes and/or enzyme combination can be studied.

The present invention also provides for the novel compounds taught herein.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
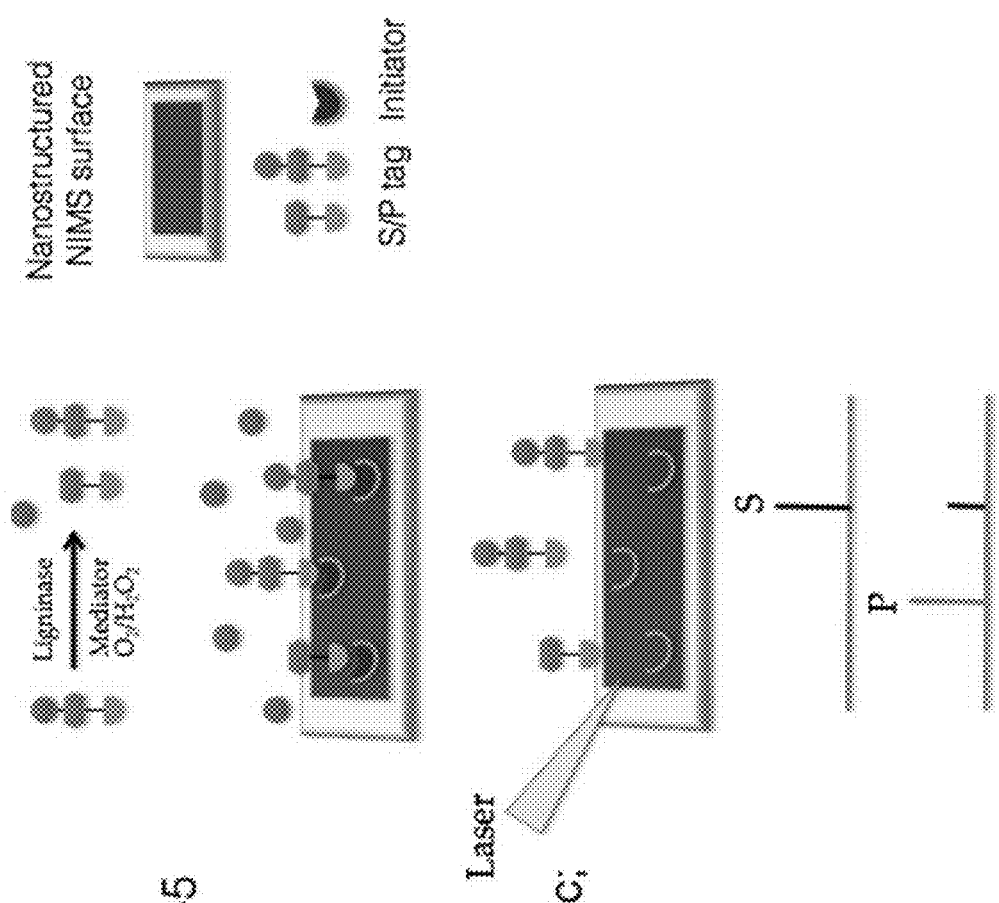
FIG. 1 shows the basic steps in the assay workflow using NIMS, including (1) NIMS substrates design; (2) performing ligninases oxidation reactions; (3) kinetics study and quantification of ratio of products to substrates.
Figure 2A:
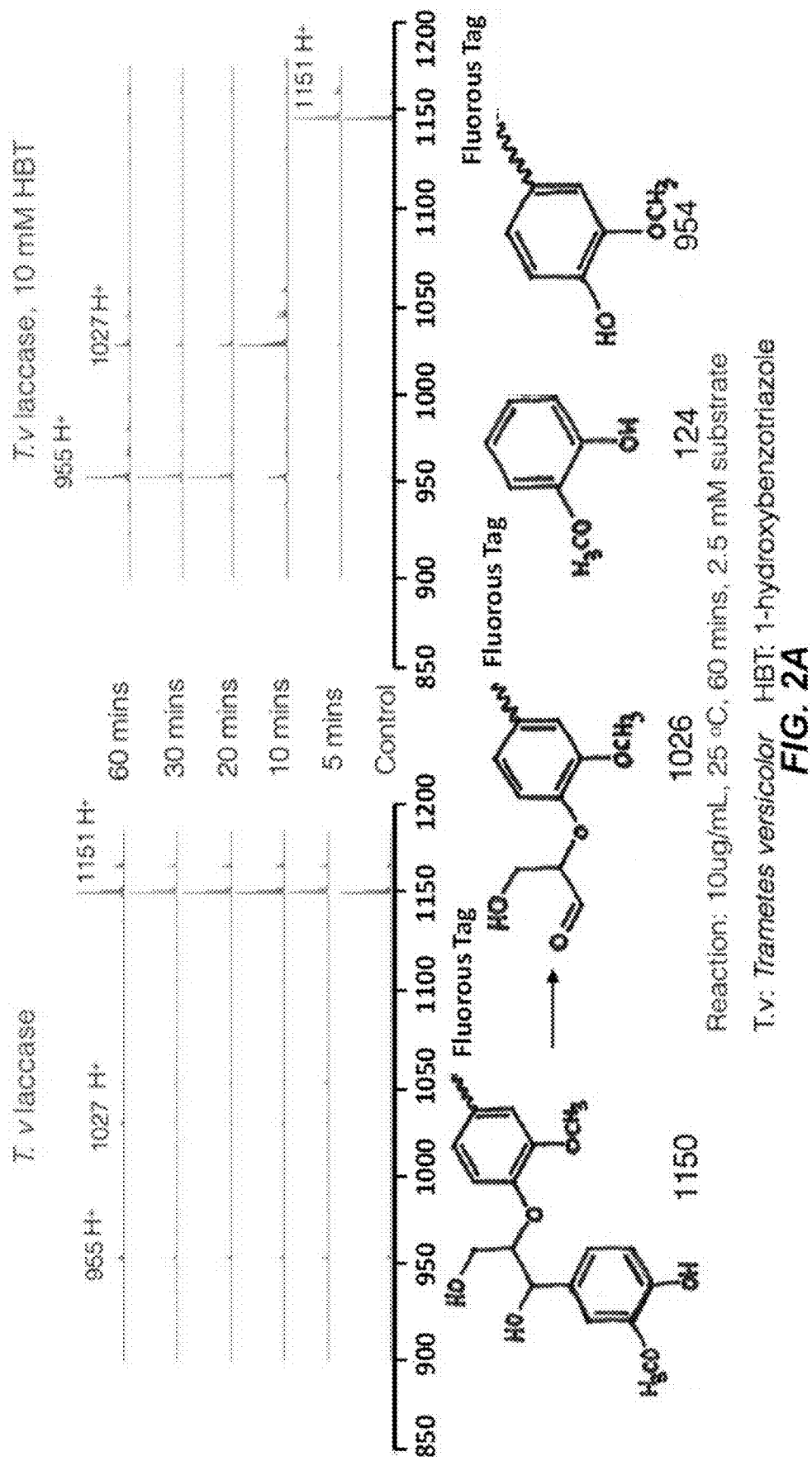
FIG. 2A shows the effect of the mediator HOBT (1-hydroxybenzotriazole) on laccase activities over time as measured using the NIMS-based assay.
Figure 2B:
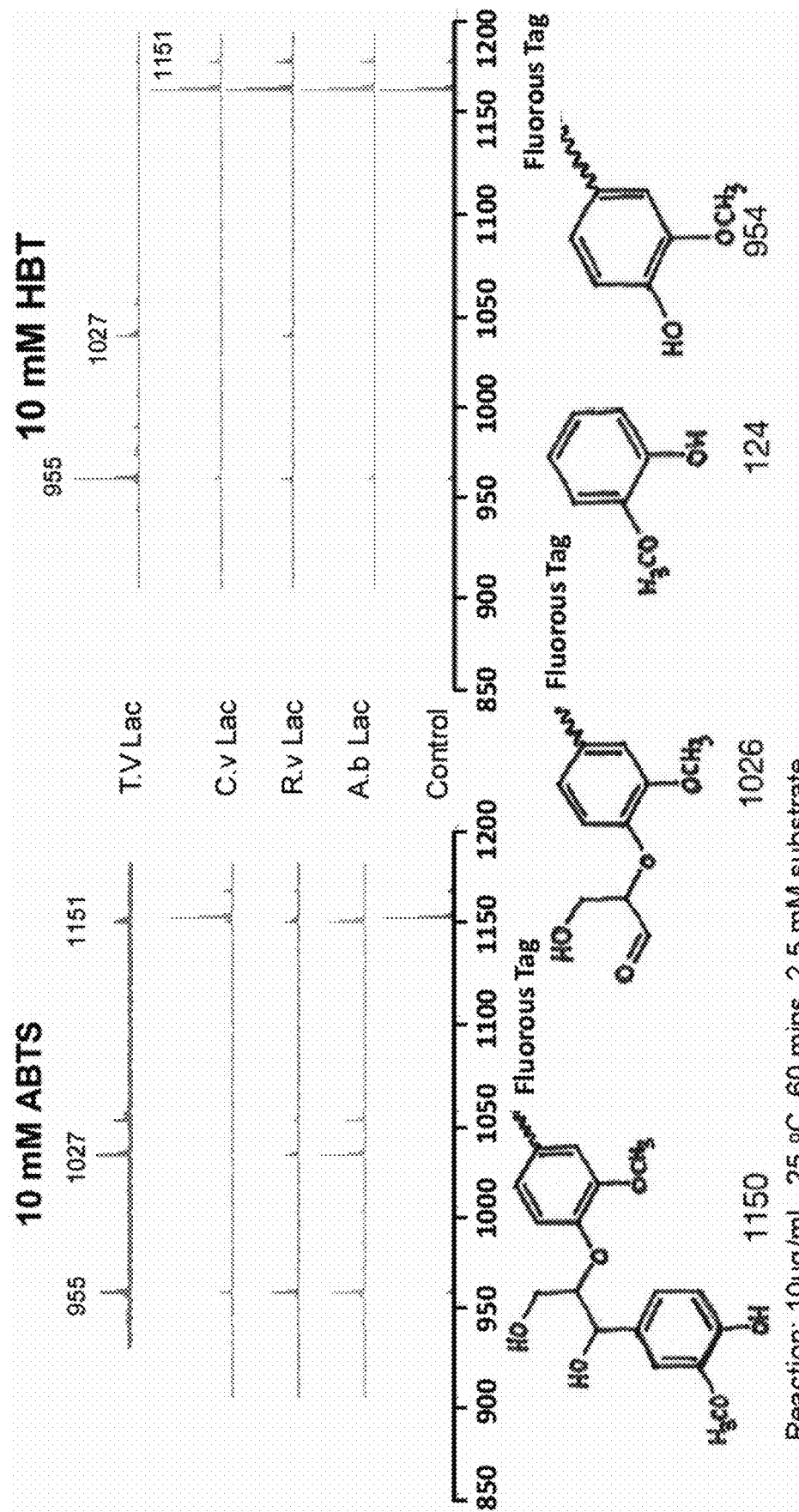
FIG. 2B shows the effect of the mediator HBT on laccase activities from various organisms as measured using the NIMS-based assay.
Figure 3:
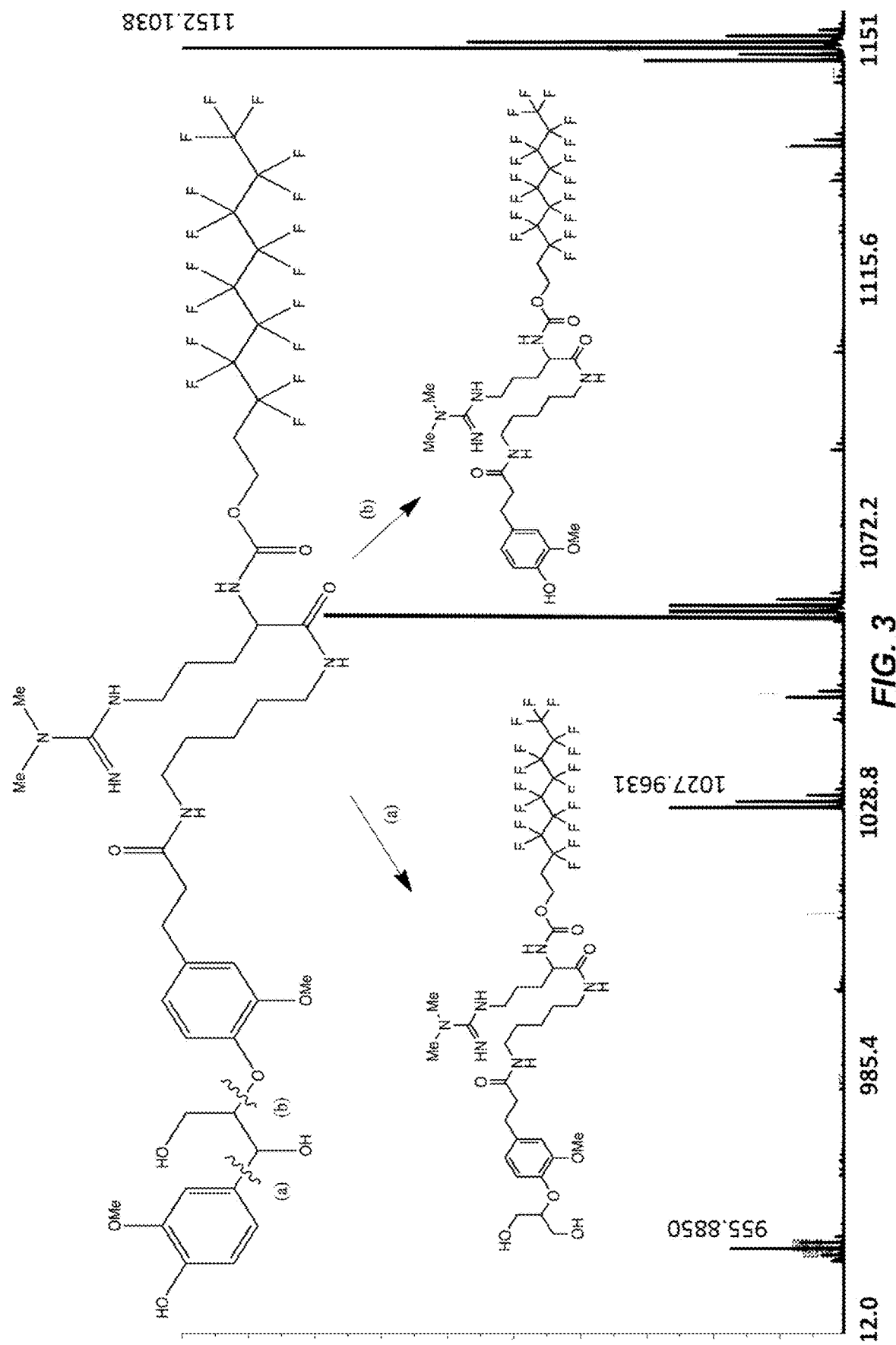
FIG. 3 shows a representative NIMS Spectra of a laccase reaction with Lignin dimer NIMS probe.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "enzyme" includes a single enzyme as well as a plurality of enzymes, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N Y 1989).

Overview

Disclosed herein are systems and methods for rapid, high throughput screening of the activities of enzymes, including ligninases and its enzyme cocktails, using mass spectrometry. In some embodiments, nanostructure initiator mass spectrometry (NIMS) surfaces, substrates and methodology are used. In some embodiments, the systems and methods disclosed herein can be used to simultaneously detect several enzymatic activities. Non-limiting exemplary applications include biofuel productions (e.g., lignocellulosic biofuel production) and chemical productions (e.g., high value chemical production).

Lignin, a major component of lignocellulosic biomass, may be an important starting material for chemical, biomaterial, or biofuel production. In some embodiments, a method disclosed herein can be used for rapid, high throughput screening. The method can comprise using nanostructure initiator mass spectrometry to find high performance enzymes such as ligninases and ligninases cocktails that can be capable of breaking down lignin, a substrate, into products that can be simpler molecules (e.g., aromatics). The high performance enzymes can be used to add value to the utilization of lignocellulosic biomass.

In some embodiments, the products of enzymatic reactions can be advantageously analyzed by NIMS, a surface based desorption ionization technique. With NIMS, only substrates and products may adhere to the surface, thus facilitating the analysis. In some embodiments, only a small percentage of non-substrates and non-products adhere to the NIMS surface. In some embodiments, the method can utilize a high throughput platform, allowing many enzymes and enzyme combinations to be studied in a rapid, high throughput manner. In some embodiments, all substrates, e.g., substrates for cellulases, hemicellulases and ligninases, can be advantageously combined together in a high throughput screening method to create assays that can simultaneously detect several enzyme activities. Compared to gas chromatography-mass spectrometry (GC-MS) and liquid chromatography-mass spectrometry (LC-MS), the method is high throughput and avoids or minimizes overlapping peaks, which may make quantitation difficult.

In some embodiments, the method can be used for identifying or determining unknown or unexpected enzyme activities in samples, such as cell culture samples and environmental samples. The enzymatic activities of one or more enzymes in a sample may be unknown. The method can be used to determine the enzymatic activities of the sample using NIMS substrates. The NIMS substrates can incorporate or simulate H, G, or S lignin units in beta-O-4 linkages, 5-5' (biphenyl), β-5 (phenylcoumaran), or 4-O-5 (diaryl ether) linkages. Each NIMS substrate may be conjugated or tagged with a unique mass fluorous tag or perfluoronated affinity moiety. The enzymatic activities of the sample can be determined using the tagged NIMS substrates. For example, an aliquot of the sample and an aliquot of the tagged NNIMS substrates can be mixed together, and the ligninases oxidation activities of the sample on the tagged NIMS substrates can be determined. The identities of the tagged NIMS reaction products can be determined and analyzed using NIMS. The enzymatic activities of the sample can be determined based on the kinetics of the enzymatic reactions and ratios of products to substrates. For example, the kinetics of the enzymatic reactions and ratios of products to substrates of the ligninases oxidation reactions can be used to determine the ligninases oxidation activities of the sample.

Substrates

In some embodiments, the NIMS substrates are designed and may incorporate or simulate lignocellulosic substrates including but not limited to H, G, or S lignin units in beta-O-4 linkages, 5-5' (biphenyl), β-5 (phenylcoumaran), 4-O-5 (diaryl ether). The NIMS substrates are tagged with a unique mass fluorous tag, and the reaction products can then be analyzed using a mass spectrometry analysis whereby individual reaction products can be identified by specific peaks due to the biomass tag. The reaction mixture is carried out on the tagged substrate. In some embodiments, the products of the reaction are then transferred to a NIMS chip. The tagged reaction products may be analyzed on the NIMS chip. In some embodiments, product to starting material mass intensity ratio (P/S) is used to determine enzyme activity on NIMS chip, and product to starting material mass intensity ratio (P/S) is used to determine enzyme activity.

The methods, compositions, and systems disclosed herein can utilize different substrates of interest to produce varying modified candidate substrates. In some embodiments, a candidate substrate can be, or comprise, a protein, a peptide, a D- or L-amino acid, a nucleic acid, a nucleotide, a nucleoside, a sugar, a primary or secondary alcohol, an aldehyde, a ketone, a catechol, a metal ion, a quinone, or a combination thereof. In some embodiments, a candidate substrate can be, or comprise, 6-mercaptopurine, cellobiose, cellotetraose, xylotetraose, isoprimeverose, β-D-gentiobiose, xyloglucan and mannotriose, or any combination thereof. In some embodiments, the one or more candidate substrate can be agarose, aminic acid, starch, oligosaccharide, polysaccharide, cellulose, ceramide, chitine, chitosan, dextrose, dextrins, fructose, fucoidan, fucose, furanoside, galactoside, glucan, glucopyranoside, glucoside, glucuronic acid, glucuronoside, glycose, glycoside, glycosaminoglycan, hexaoside, inulin, lactose, levanose, lipopolysaccharide, mannose, maltoside, maltotrioside, mannose, octulosonate, oligosaccharide, pectate, pectin, peptide, polygalacturonide, polynucleotides, pullulan, rhamnoside, xylan, or any combination thereof.

Candidate substrates can differ from one another. In some embodiments, candidate substrates can differ from one another by at least one functional group. The at least one functional group can be alkyl, alkenyl, alkynyl, phenyl, benzyl, halo, fluoro, chloro, bromo, iodo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, acetal, orthoester, methylenedioxy, orthocarbonate ester, carboxamide, primary amine, secondary amine, tertiary amine, 4° ammonium, primary ketamine, secondary ketamine, primary aldimine, secondary aldimine, imide, azide, azo, diimide, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothione, carbonothial, phosphino, phosphono, phosphate, phosphodiester, borono, boronate, borino, or borinate. In some embodiments, candidate substrates can differ from one another by or by about 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, Daltons. In some embodiments, candidate substrates can differ from one another by at least or by at most 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, Daltons.

Candidate substrates and modified candidate substrates can have different structures and molecular weights. A substrate of interest and a modified substrate of interest can have different structures and molecular weights. In some embodiments, a candidate substrate or a substrate of interest can differ from its corresponding modified substrate by at least one functional group. In some embodiments, a candidate substrate or a substrate of interest can differ from its corresponding modified substrate by or by about 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, Daltons. In some embodiments, a candidate substrate can differ from its corresponding candidate modified candidate by at least or by at most 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values, Daltons.

Enzymes

Any enzyme having an activity that changes the mass of a substrate can serve as an enzyme of interest in the embodiments described herein. An enzyme to be screened is reacted with a starting crude heterogeneous mixture such as biomass or other native glycans.

In some embodiments, the enzyme of interest is involved in sugar modification. For example, the enzyme of interest can have an activity related to changing the chain length of a sugar head group. For example, enzymes of interest include enzymes that cleave off one or more sugar monomers (glycohydrolases) or enzymes that extend the sugar head group by attaching one or more sugar units (glycotransferases). Without limitation, several classes of enzymes of interest in the embodiments of the present invention include glycohydrolases, glycotransferases, endoglucanases, exoglucanases, and hemicellulases.

In some embodiments, the enzyme of interest reduces the chain length of a sugar head group. In certain aspects, the enzyme of interest is an endoglucanase, exoglucanase, glucosidase and/or hemicellulase. In various embodiments, the sugar includes cellulose, hemicellulose, xylose, cellobiose, cellotetraose, or xylobiose. In some embodiments, the enzyme degrades plant cell wall and/or lignin. In certain aspects, the enzyme is a laccase or peroxidase.

In other embodiments, the enzyme of interest is an enzyme in other biochemical or metabolic pathways of other organisms and not involved in degrading sugars. Enzymes may include but are not limited to acetyltransferases, transferases, carboxylases, isomerases, anhydrases, dismutases, catalases, esterases, fumarase, lactases, lactamases, phosphatases, kinases, reductases, oxidases, cellulases, proteases, amylases, hydroxylases, polymerases, dehydrogenases, trypsin, lipases, amylases, xylinases, synthetases, ligases and restriction enzymes.

In another embodiment, the enzyme of interest is a modified or non-naturally occurring enzyme which has been mutated or engineered to provide different, altered, or improved function and/or activity.

In some embodiments, the enzyme of interest and/or their co-enzymes, cofactors, inhibitors or catalysts may also be included in the mixture and screened using the present methods. In another embodiment, for hydrolytic enzyme library screening, if incomplete hydrolysis is observed upon screening a first enzyme, the mixture can be screened for additional enzymes that would complete the hydrolysis. Enzymes can be added to the cocktail until the desired conversion of biomass is achieved.

The methods, compositions, and systems disclosed herein can be used to test different enzymes of interest. In some embodiments, the enzymes can be, or can include, Enzyme Commission (EC) 1 oxidoreductases (e.g., a dehydrogenase or an oxidase); EC 2 transferases (e.g., a transaminase or a kinase); EC 3 Hydrolases (e.g., a lipase, an amylase, or a peptidase); EC 4 Lyases (e.g., a decarboxylase); EC 5 Isomerases (e.g., an isomerase or a mutase); or EC 6 Ligases (e.g., a synthetase).

In some embodiments, the enzymes of interest can be, or can include, EC 1.1 oxidoreductases acting on the CH—OH group of donors; EC 1.2 oxidoreductases acting on the aldehyde or oxo group of donors; EC 1.3 oxidoreductases acting on the CH—CH group of donors; EC 1.4 oxidoreductases acting on the CH—NH(2) group of donors; EC 1.5 oxidoreductases acting on the CH—NH group of donors; EC 1.6 oxidoreductases acting on NADH or NADPH; EC 1.7 oxidoreductases acting on other nitrogenous compounds as donors; EC 1.8 oxidoreductases acting on a sulfur group of donors; EC 1.9 oxidoreductases acting on a heme group of donors; EC 1.10 oxidoreductases acting on diphenols and related substances as donors; EC 1.16 oxidoreductases oxidizing metal ions; EC 1.17 oxidoreductases acting on CH or CH(2) groups; EC 1.18 oxidoreductases acting on iron-sulfur proteins as donors; EC 1.19 oxidoreductases acting on reduced flavodoxin as donor; EC 1.20 oxidoreductases acting on phosphorus or arsenic in donors; EC 1.21 oxidoreductases catalyzing the reaction X—H+Y—H='X—Y'; EC 1.22 oxidoreductases acting on halogen in donors; EC 1.23 oxidoreductases reducing C—O—C group as acceptor; or EC 1.97 other oxidoreductases.

In some embodiments, the enzymes of interest can be, or can include, EC 2.1 transferases transferring one-carbon groups with substrates: DNA, RNA, catechol; EC 2.2 transferases transferring aldehyde or ketonic groups; EC 2.3 acyltransferases; EC 2.4 glycosyltransferases; EC 2.5 transferases transferring alkyl or aryl groups, other than methyl groups; EC 2.6 transferases transferring nitrogenous groups; EC 2.7 transferases transferring phosphorus-containing groups; EC 2.8 transferases transferring sulfur-containing groups; EC 2.9 transferases transferring selenium-containing groups; or EC 2.10 transferases transferring molybdenum- or tungsten-containing groups.

In some embodiments, the enzymes of interests can be, or can include, EC 3.1 hydrolases acting on ester bonds; EC 3.2 glycosylases; EC 3.3 hydrolases acting on ether bonds; EC 3.4 hydrolases acting on peptide bonds (peptidases); EC 3.5 hydrolases acting on carbon-nitrogen bonds, other than peptide bonds; EC 3.6 hydrolases acting on acid anhydrides; EC 3.7 hydrolases acting on carbon-carbon bonds; EC 3.8 hydrolases acting on halide bonds; EC 3.9 hydrolases acting on phosphorus-nitrogen bonds; EC 3.10 hydrolases acting on sulfur-nitrogen bonds; EC 3.11 hydrolases acting on carbon-phosphorus bonds; EC 3.12 hydrolases acting on sulfur-sulfur bonds; or EC 3.13 hydrolases acting on carbon-sulfur bonds.

In some embodiments, the enzymes of interests can be, or can include, glycosyl hydrolases (enzymes that are useful for breaking down plant biomass for the production of biofuels), aminotransferases (proteins that are involved in binding and transport of small organic molecules or proteins that are important for biomanufacturing), solute binding proteins of ATP-binding cassette (ABC) transporter proteins (proteins involved in the metabolism of soil microbes with a potential impact in bioremediation), or any combination thereof.

In some embodiments, the enzymes of interests can be, or can include, EC 4.1 carbon-carbon lyases; EC 4.2 carbon-oxygen lyases; EC 4.3 carbon-nitrogen lyases; EC 4.4 carbon-sulfur lyases; EC 4.5 carbon-halide lyases; EC 4.6 phosphorus-oxygen lyases; EC 4.7 carbon-phosphorus lyases; or EC 4.99 other lyases.

In some embodiments, the enzymes of interests can be, or can include, EC 6.1 ligases forming carbon-oxygen bonds; EC 6.2 ligases forming carbon-sulfur bonds; EC 6.3 ligases forming carbon-nitrogen bonds; EC 6.4 ligases forming carbon-carbon bonds; EC 6.5 ligases forming phosphoric ester bonds; or EC 6.6 ligases forming nitrogen-metal bonds.

In some embodiments, the enzyme can be a methyltransferase or a glycoside hydrolase. In some embodiments, the enzyme can be a agarase, a aminidase, a amylase, a biosidase, a carrageenase, a cellulase, a ceramidase, a chitinase, a chitosanase, a citrinase, a dextranase, a dextrinase, a fructosidase, a fucoidanase, a fucosidase, a furanosidase, a galactosidase, a galacturonase, a glucanase, a glucosidase, a glucuronidase, a glucuronosidase, a glycohydrolase, a glycosidase, a hexaosidase, a hydrolase, an iduronidase, a inosidase, an inulinase, a lactase, a levanase, a licheninase, a ligase, a lyase, a lysozyme, a maltosidase, a maltotriosidase, a mannobiosidase, a mannosidase, a muramidase, an octulosonase, an octulosonidase, a primeverosidase, a protease, a pullulanase, a rhamnosidase, a saminidase, a sialidase, a synthase, a transferase, a trehalase, a turonidase, a turonosidase, a xylanase, or a xylosidase.

The number of enzymes of interests tested can vary. In some embodiments, the number of enzymes tested can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, $10^9$, or a number or a range between any two of these values. In some embodiments, the number of enzymes tested can be at least or can be at most 1, 2, 3, 4, 5, 6, 7, 8, 9, 10, 20, 30, 40, 50, 60, 70, 80, 90, 100, 200, 300, 400, 500, 600, 700, 800, 900, 1000, $10^4$, $10^5$, $10^6$, $10^7$, $10^8$, or $10^9$.

Samples

In some embodiments, a sample can contain one or more enzymes of interest. In some embodiments, the sample is a biological sample, a clinical sample, an agricultural sample, an industrial sample, an environmental sample, a ground water sample, a regional species pool, or any combination thereof. Biological samples may be derived from human or other animals, body fluid, solid tissue samples, tissue cultures or cells derived therefrom and the progeny thereof, sections or smears prepared from any of these sources, or any other samples that contain nucleic acids. Non-limiting examples of a clinical sample include urine, blood, cerebrospinal fluid, spinal fluid, sinovial fluid, semen, ammoniac fluid, cerebrospinal fluid (CSF), and saliva. A biological sample can include, for example, food products and ingredients such as dairy items, vegetables, meat and meat by-products, and waste. Environmental samples can be derived from environmental material including but not limited to soil, water, sewage, cosmetic, agricultural and industrial samples, as well as samples obtained from food and dairy processing instruments, apparatus, equipment, disposable, and non-disposable items.

Enzymatic Reactions

The methods also can screen for development or optimization of enzyme cocktail recipes. Various cocktails can be screened quickly to optimize and vary the ratio of enzymes in the cocktail, the optimal time to add an enzyme to the cocktail, etc. until the desired conversion of biomass is achieved. Thus, in some embodiments, the present methods may provide for enzyme cocktail optimization by providing fast, efficient analysis of native laccases using high specificity mass spectrometry based enzyme assays.

In some embodiments, mediators, pH, buffer, bi-phase solvents and other reaction reagents are added to the reaction.

Enzymatic reactions can be carried out in solution using test tubes or microwell microtiter plates (96-well, 384-well). Enzymatic reactions can be performed using the amphiphilic substrate analogs in standard reaction tubes or plates where all reaction conditions can easily be controlled. Various embodiments described herein involve a solution-based assay system that can be applied to all kinds of standard reaction tubes and microtiter plates. Furthermore, all liquid handling and sample spotting can be interfaced with existing pipetting robots and liquid handling systems, so that several described embodiments are highly suitable for high-throughput applications.

Mass Spectrometry

The reaction products can then be analyzed using a mass spectrometry analysis whereby individual reaction products can be identified by specific peaks due to the biomass tag. Suitable analysis methods may include but are not limited to matrix-assisted laser desorption ionization (MALDI), nanoparticle initiator mass spectrometry (NIMS) and secondary ion mass spectrometry (SIMS); Laser Desorption; Desorption ElectroSpray Ionization (DESI); Probe ElectroSpray Ionization (PESI); or Laser Spray. Various instrument modalities may include but are not limited to time-of-flight (TOF), Orbitrap, Fourier-transform ion cyclotron (FTIR), magnetic sector, quadrupole, or other mass spectrometers. In a preferred embodiment, tandem mass spectrometers (MS/MS) are used, such as TOF-TOF or Quadrupole-TOF, wherein the second MS collects fragmentation spectra for molecular characterization of ions analyzed by the first mass spectrometer.

In various embodiments, the mass of the reaction product generated by incubating a sample or enzyme with a substrate can be determined by nanostructure-initiator mass spectrometry (NIMS). NIMS is described in T. R. Northen, O. Yanes, M. T. Northen, D. Marrinucci, W. Uritboonthai, J. Apon, S. L. Golledge, A. Nordstrom, G. Siuzdak, *Nature* 2007, 449, 1033-1036; T. R. Northen, J. C. Lee, L. Hoang, J. Raymond, D. R. Hwang, S. M. Yannone, C. H. Wong, G. Siuzdak, *Proc. Natl. Acad. Sci. USA* 2008, 105, 3678-3683; PCT International Patyent Application Nos. PCT/US2012/054329 and PCT/US2016/055536; U.S. Patent Application Publication Nos. 2008/0128608, 2012/0225797, 2014/0247115, 2014/0329274, and 2015/0330992; and U.S. Pat. Nos. 9,082,600; 9,125,596; and 9,460,904; which are herein fully incorporated by reference. Production of NIMS chips is described in detail in H. K. Woo, T. R. Northen, O. Yanes, G. Siuzdak, *Nat. Protoc.* 2008, 3, 1341-1349, which is herein fully incorporated by reference. The ratio of substrate-to-reaction product ions in the mass spectrum can be analyzed to determine the presence of the enzyme of interest in the sample.

The present invention also provides for the methods and compounds/probes/substrates of the present invention adapted or used to modify any of the inventions taught in the patents and patent applications incorporated herein.

A variety of apparatuses may be used in NIMS to measure the mass-to-charge ratio of the ionized target. For example, in several embodiments a time-of-flight mass analyzer is used for measuring the desorbed and ionized target. However, other non-limiting examples of mass analyzers that can be used include magnetic ion cyclotron resonance instruments, deflection instruments, and quadrupole mass analyzers.

The present method further integrates novel organic synthesis strategies, robotic automation and mass imaging data analysis. Multiplexing assays development will significantly increase the throughput of these assays which will in turn allow for generation of more cost effective production of biofuels (e.g., lignocellulosic biofuels) and high value chemicals.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Chemical Probes for Studying Lignin Deconstruction and Analysis of Biofuel Molecules Using Nanostructure-Initiator Mass Spectrometry (NIMS)

Lignocellulosic biomass is composed of carbohydrate polymers (cellulose, hemicellulose) and an aromatic polymer (lignin). The complexity of the biomass structure requires cost effective enzyme cocktails for its deconstruction. In addition, a robust method to screen biofuel-producing strains for desired products is needed to support development and optimization of strains with high titre productivity. In order to meet these crucial challenges, mass spectrometry based assays with high-throughput, small sample volume, good sensitivity and importantly, adaptability to automated workstations to facilitate study large enzyme or microbial library strain libraries is developed. Central to this approach is to use synthetic organic chemistry to prepare chemical probes that enhance nanostructure-initiator mass spectrometry (NIMS) based analysis. This includes model substrates suitable for screening the activities of cellulases, hemicellulases and ligninases. This example focuses on the development of model substrates to study ligninases and various chemical probes to detect primary amine containing products (peptides, proteins), carboxylic acid (e.g. fatty acid), ketones and alcohol products (1-butanol, 3-methyl-3-butenol, fatty alcohol et. al) from biofuel production strains.

Development of Beta-Aryl Ether Dimer Model Compounds to Study Ligninases

To 10 µL of phenolic or non-phenolic beta-aryl ether NIMS probe (1 mM in D.I. water) is added 1 µL of laccase (2 mg/mL in 100 mM of pH 4.6 sodium acetate buffer). 1 µL of HOBt (100 mM solution) is added for nonphenolic substrate as well. The assay is incubated at 37° C. for 1 h. NIMS analysis shows the products profiles.

Figure 4:
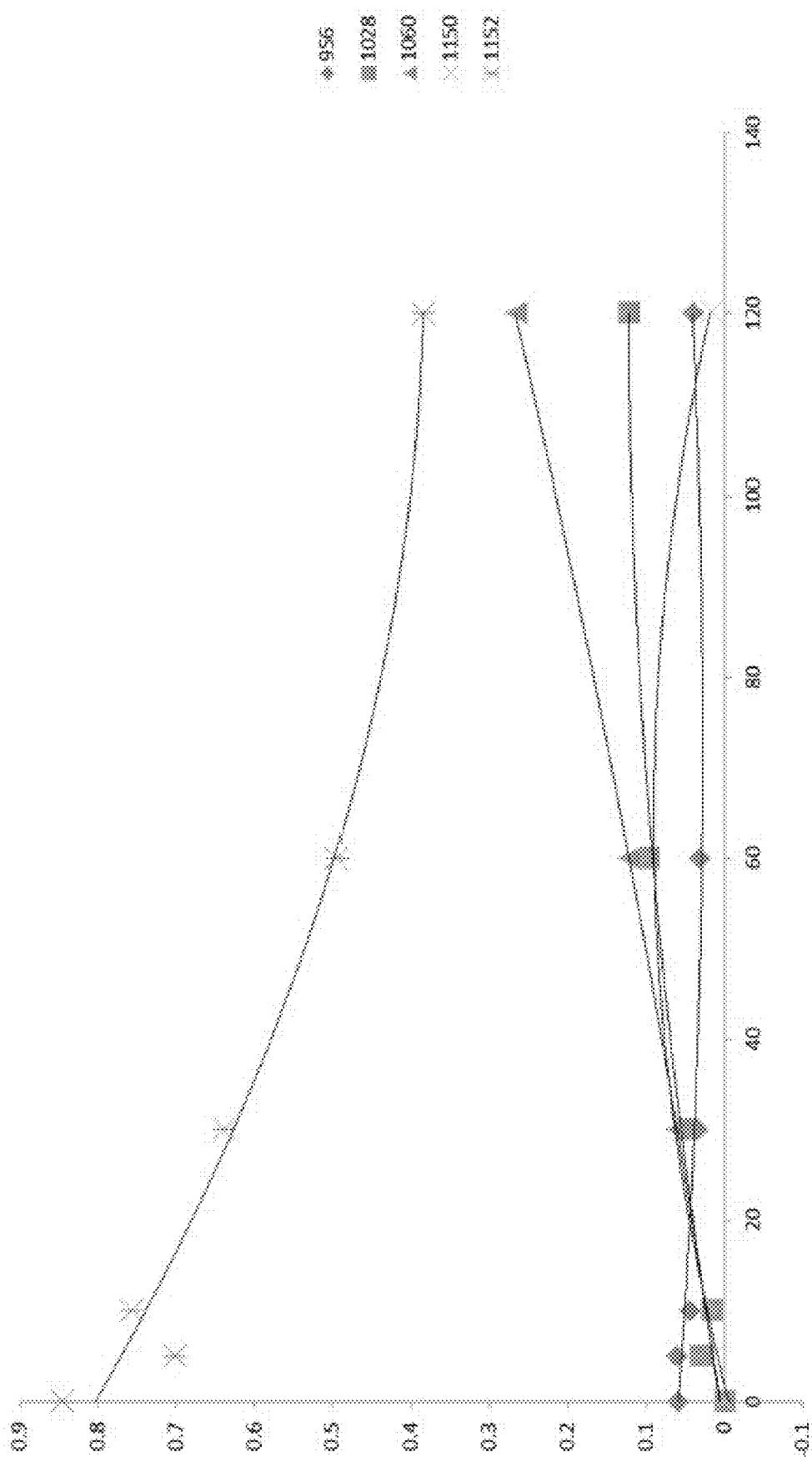
FIG. 4 shows a graph of a time course of a laccase reaction with lignin dimer NIMS probe.
Figure 5:
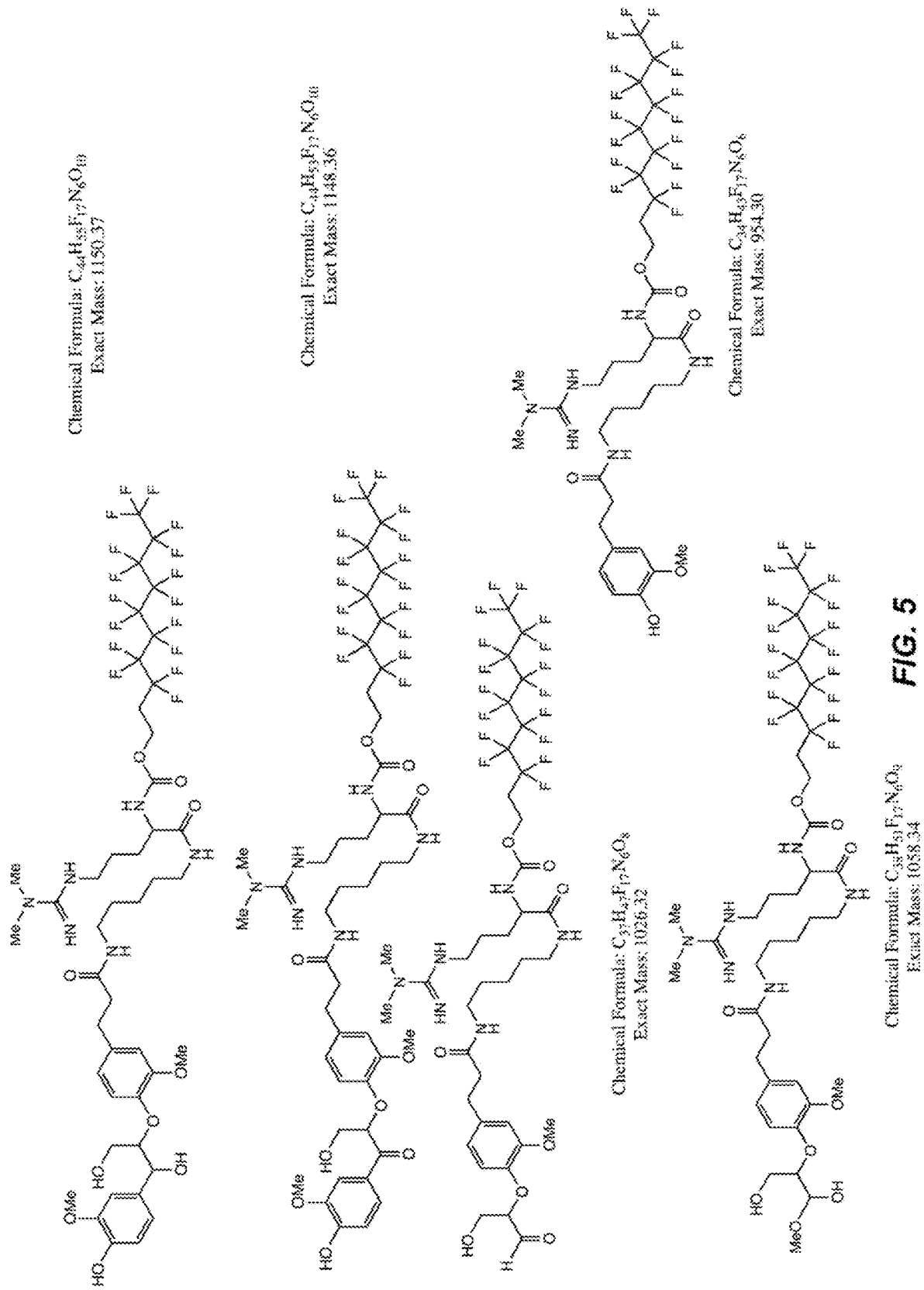
FIG. 5 shows a potential products list from the reaction of laccase with lignin dimer NIMS probe.
Figure 9A:
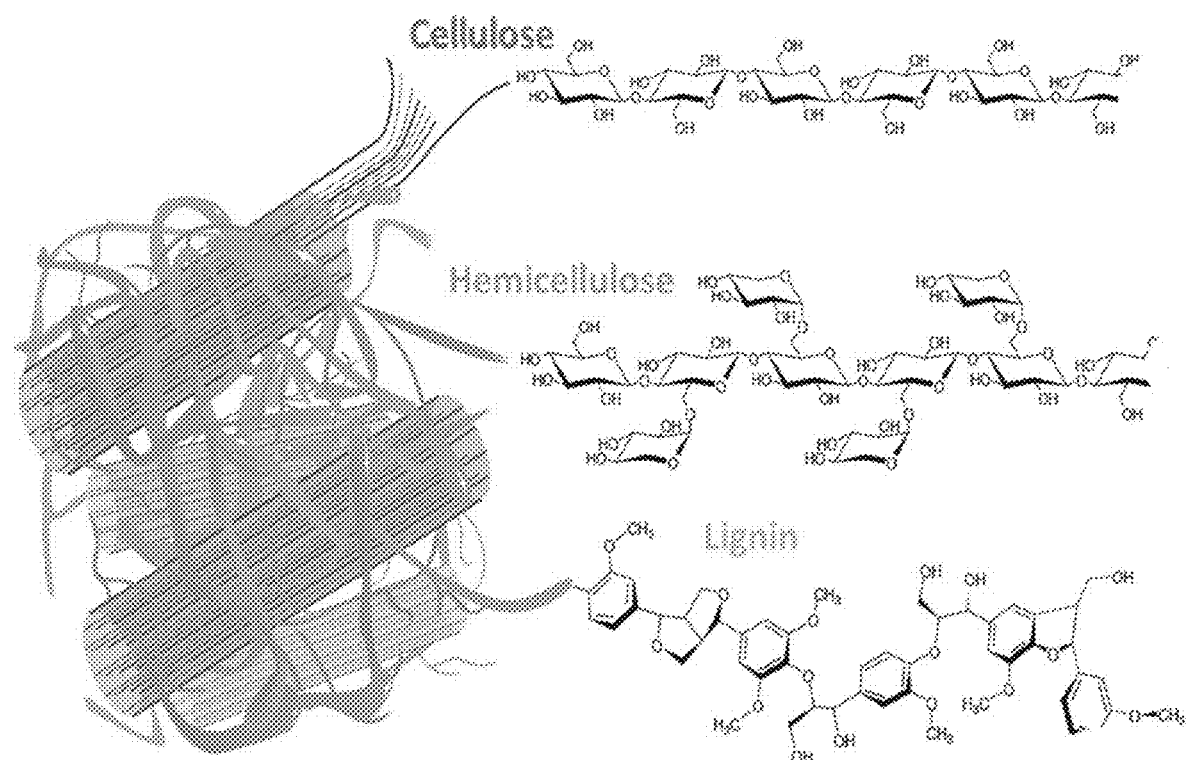
FIG. 9A shows the structures of cellulose, hemicellulose and lignin in biomass.
Figure 9B:
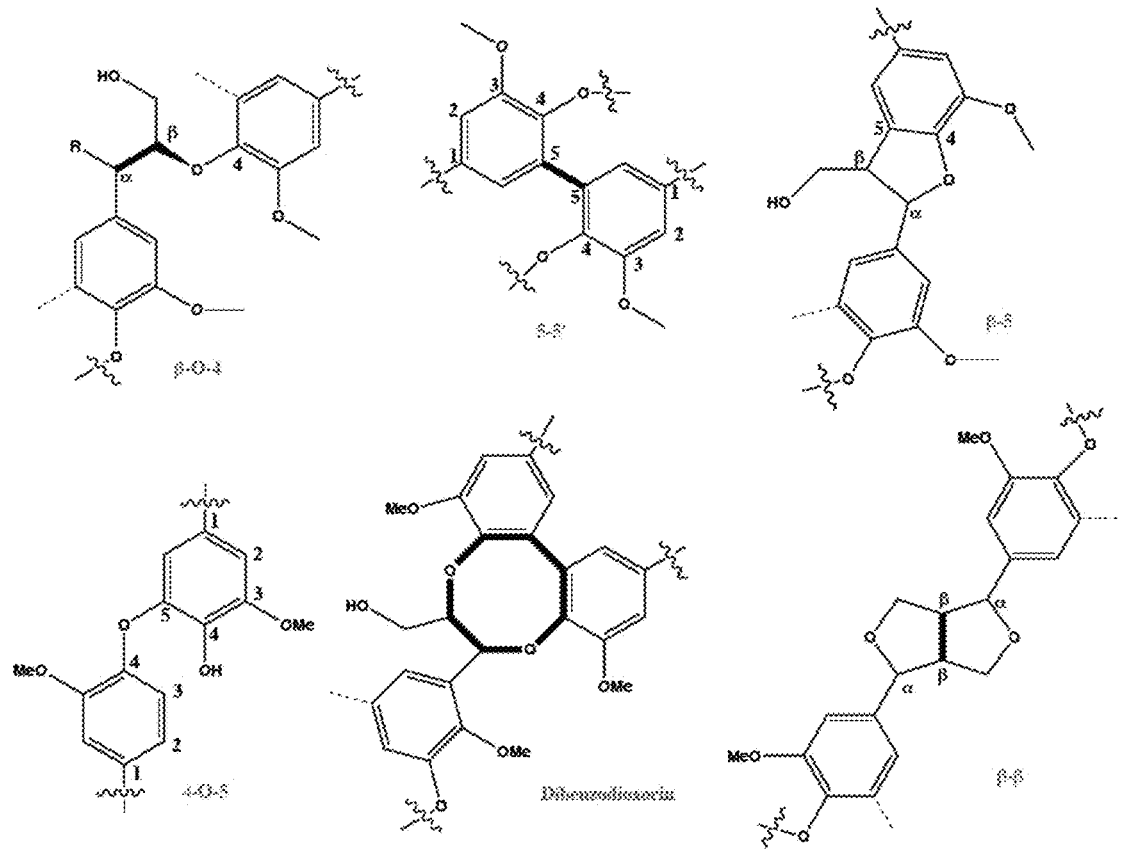
FIG. 9B shows the common linkages found in lignin in biomass.
Figure 10:
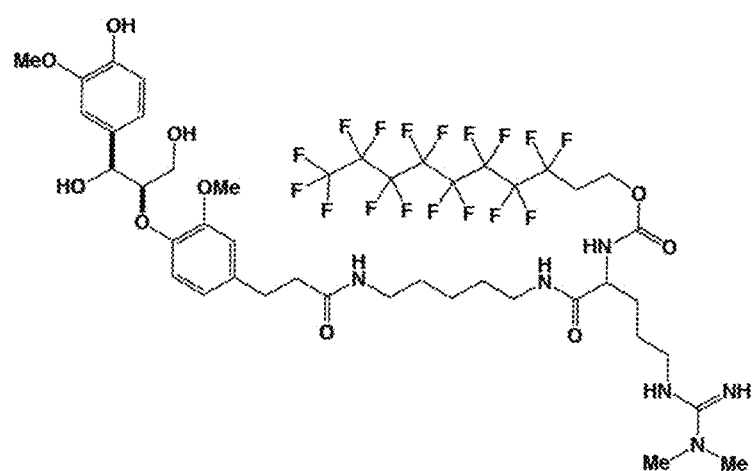
FIG. 10 shows a phenolic beta-aryl ether dimer NIMS substrate and the reactions of phenolic substrate with laccase, MnP. Both enzymes cleave alpha bonds, rather than of beta bond. This results support the formation of phenolic radical first in the reaction pathway.
Figure 10:
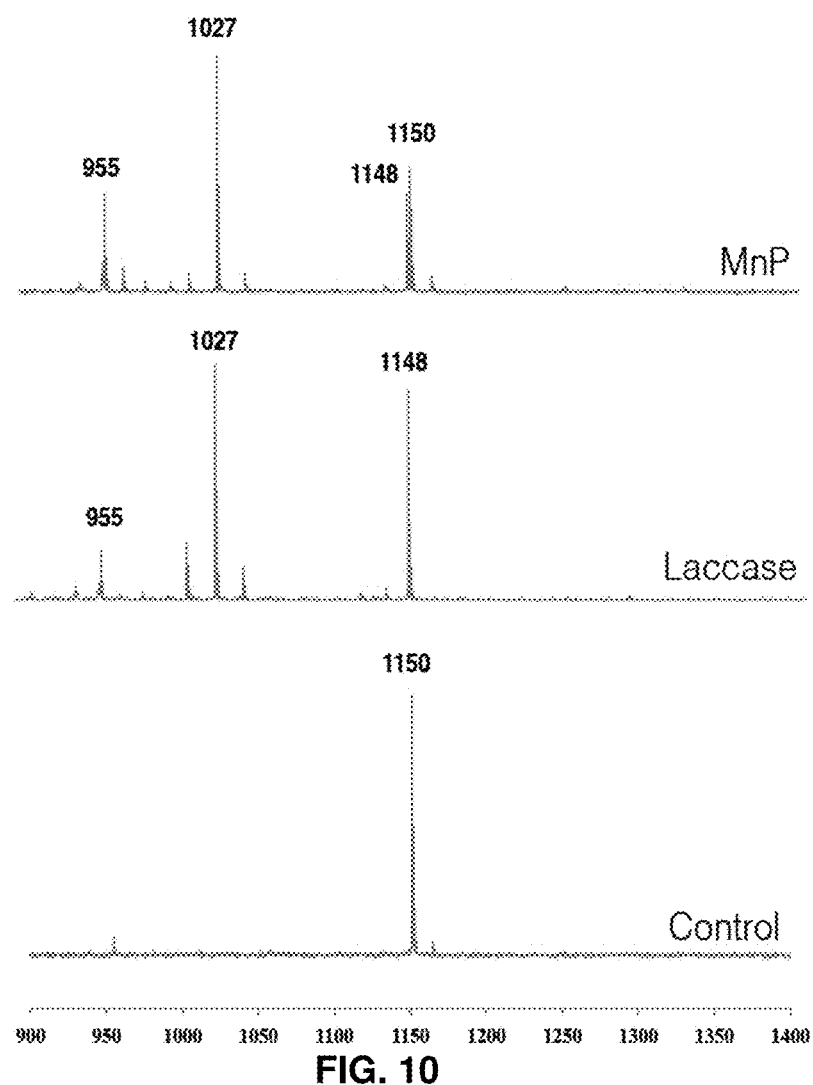
Figure 11:
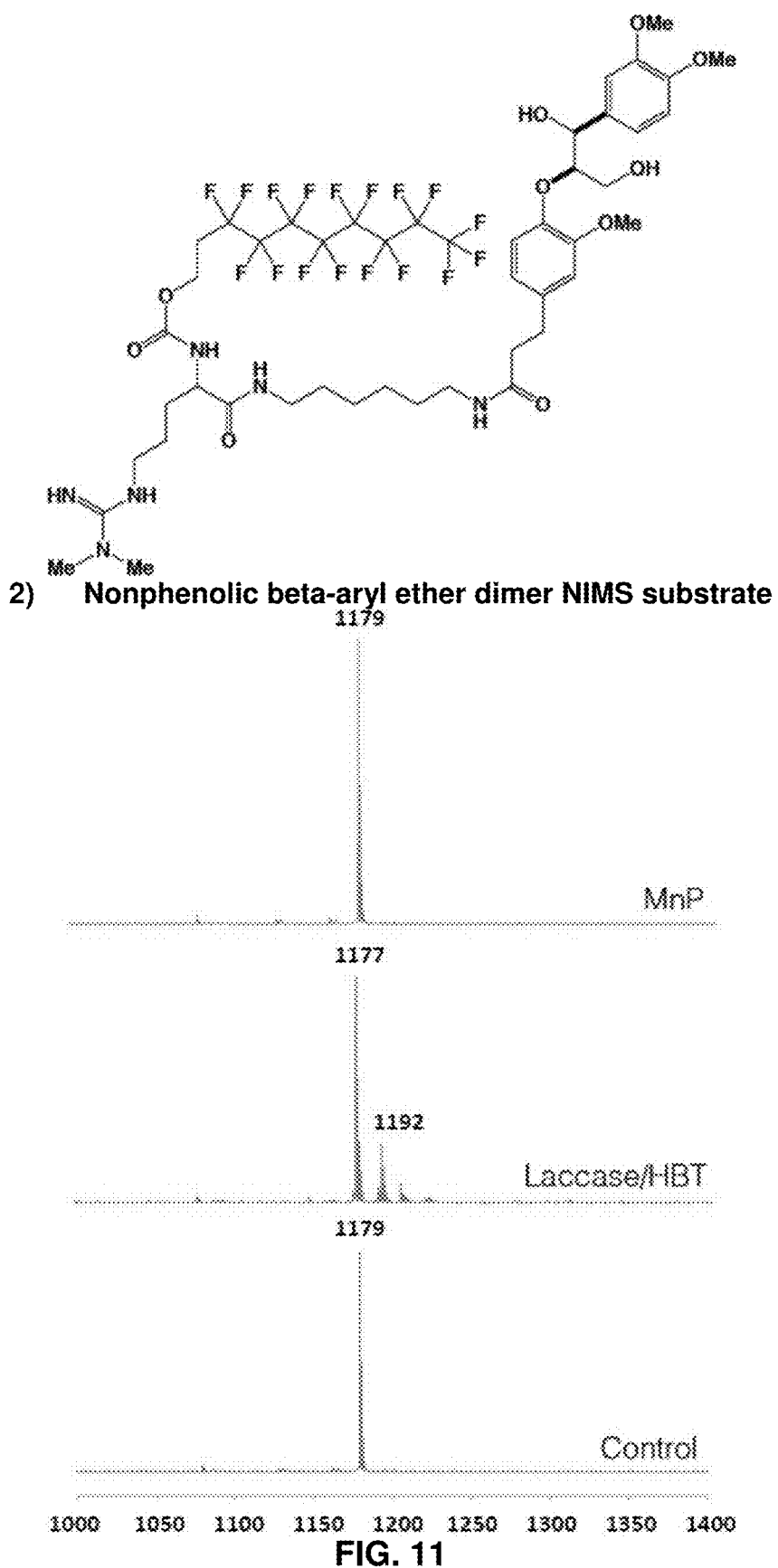
FIG. 11 shows a non-phenolic beta-aryl ether dimer NIMS substrate and reactions of nonphenolic substrate with laccase, MnP. Both enzymes cleave alpha bonds, rather than of beta bond. This results support the formation of phenolic radical first in the reaction pathway.
Figure 12:
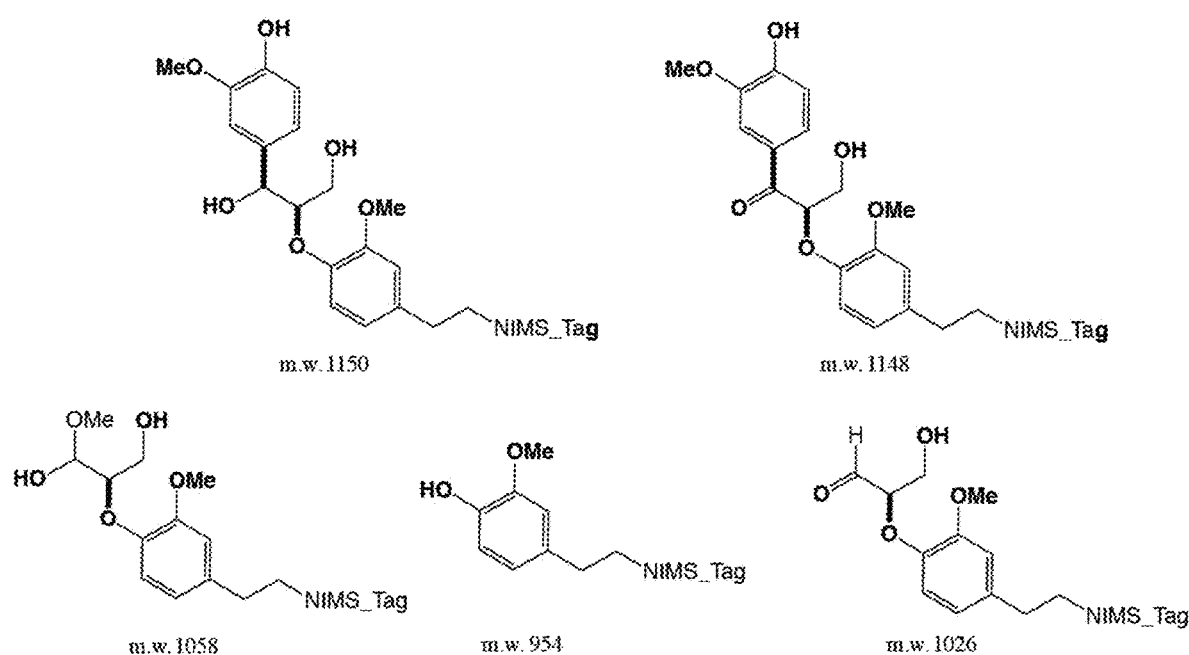
FIG. 12 shows exemplary phenolic beta-arylether dimer NIMS probes.

FIGS. 9A and 9B provide model substrates to study ligninases. FIGS. 10 and 11 provide model substrates and reactions of phenolic and non-phenolic substrates with laccase, MnP. FIGS. 4 and 12 show the time course of a laccase reaction with phenolic beta-arylether dimer NIMS probe.

Figure 6A:
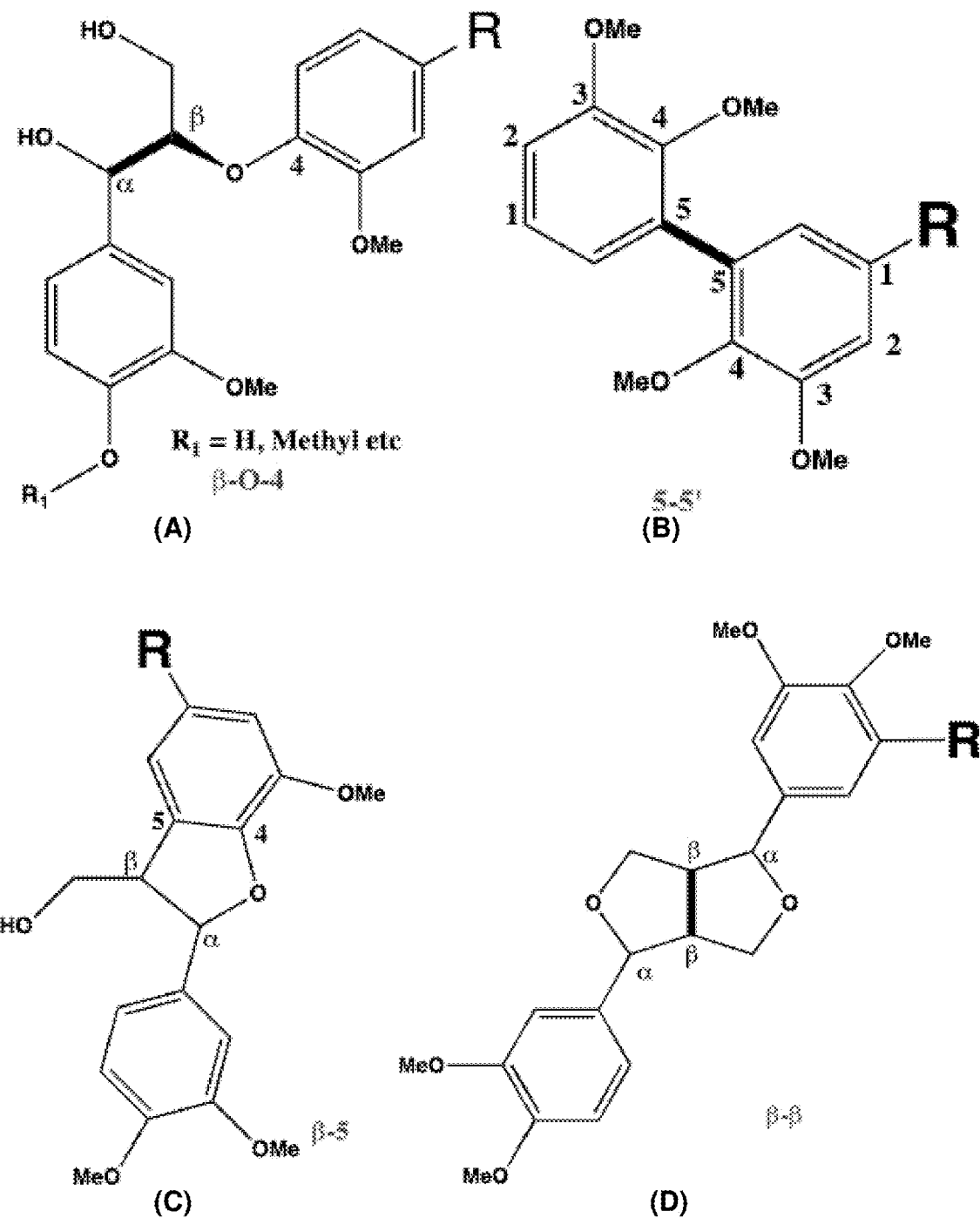
FIG. 6A shows exemplary probes for studying the activity of ligninases. The chemical structures are labeled compounds (A) to (D). The R groups are labeled 1a and 1b in FIG. 6B.
Figure 6B:
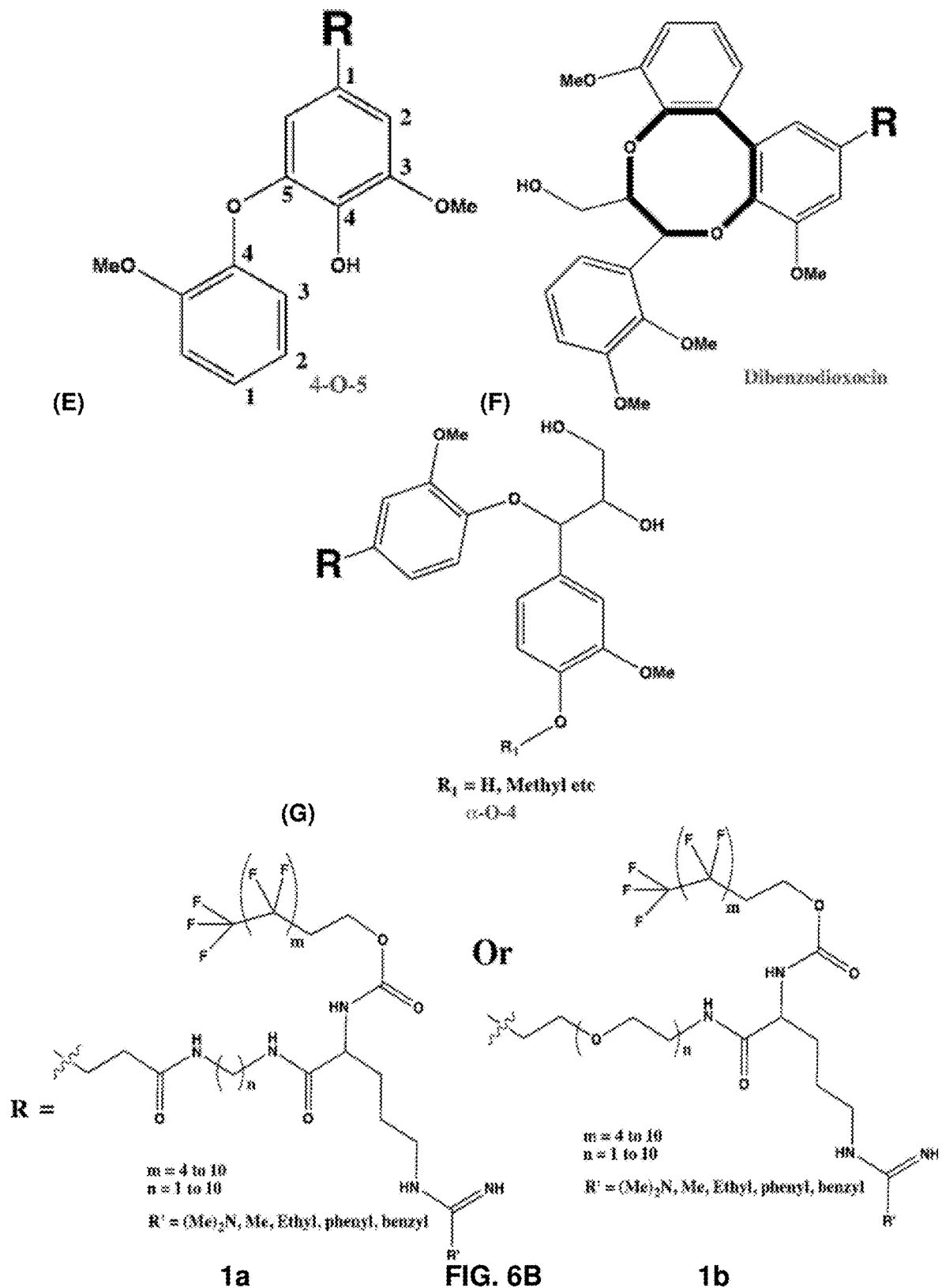
FIG. 6B shows exemplary probes for studying the activity of ligninases. The chemical structures are labeled compounds (E) to (G). The R groups are labeled 1a and 1b.
Figure 7:
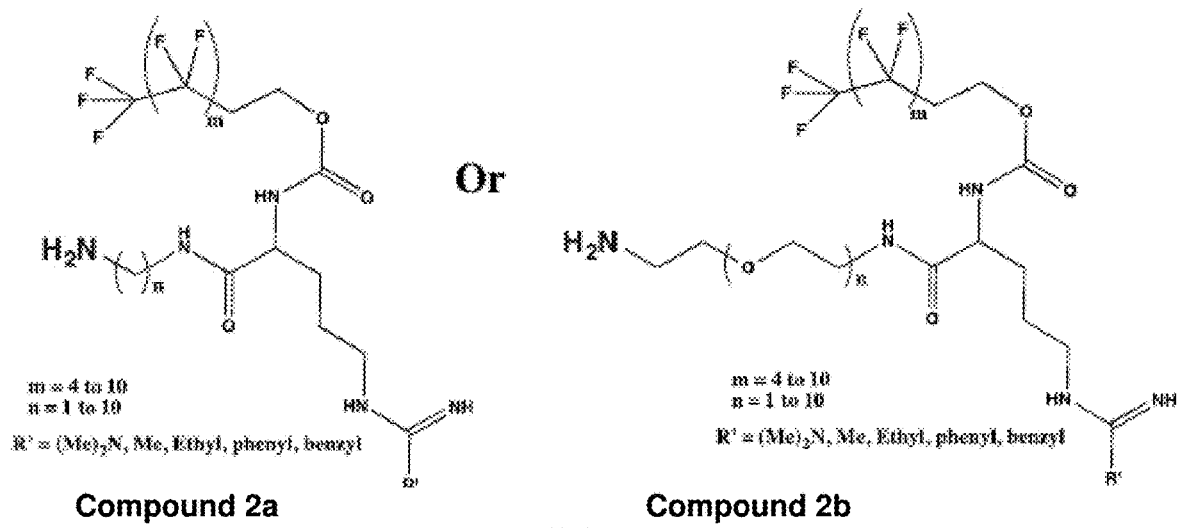
FIG. 7 shows exemplary probes for the capture of carboxylic acid. The chemical structures are labeled compounds 2a and 2b.
Figure 8:
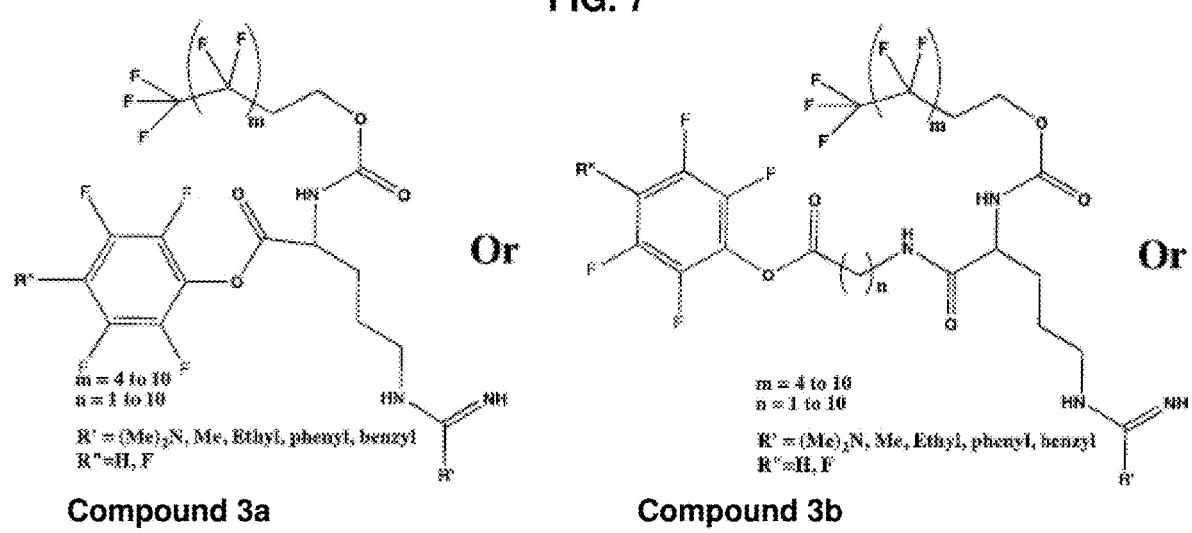
FIG. 8 shows exemplary probes for the capture of peptides/proteins. The chemical structures are labeled compounds 3a, 3b and 3c.
Figure 8:
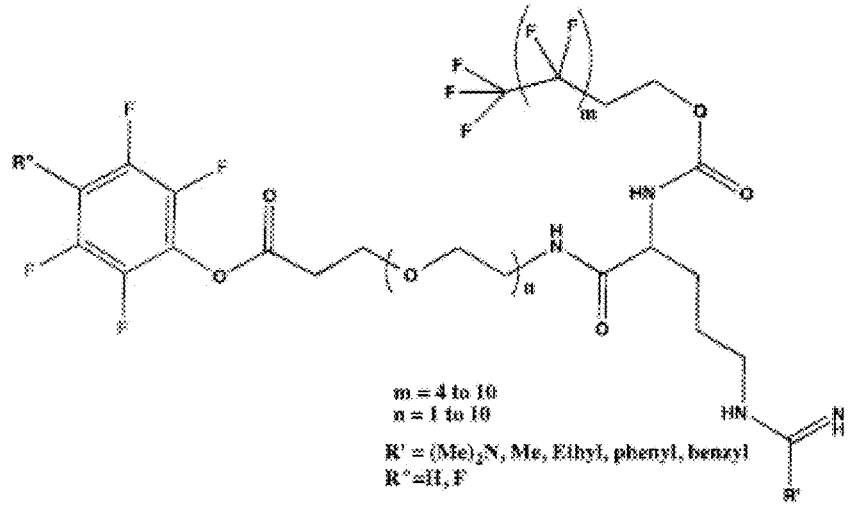

Exemplary probes are shown in FIG. 6A and FIG. 6B. Exemplary compounds are shown in Table 1:

TABLE 1

Exemplary probes for studying the activity of ligninases.

|  | (A) | (B) | (C) | (D) | (E) | (F) | (G) |
|---|---|---|---|---|---|---|---|
| R = 1a | Compound A-1a | Compound B-1a | Compound C-1a | Compound D-1a | Compound E-1a | Compound F-1a | Compound G-1a |
| R = 1b | Compound A-1b | Compound B-1b | Compound C-1b | Compound D-1b | Compound E-1b | Compound F-1b | Compound G-1b |

Capture of Carboxylic Acid 10 mg of the acid-capture probe is dissolved in 130 μL of a mixture of DMF/dioxane/H$_2$O=2:2:1 to make a 0.1M stock solution. To 10 μL of above solution in an Eppendoff vial is added 1 μL of diisopropylethylamine (DIPEA) followed by 1 μL of carboxylic acid (e.g. acetic acid). After the addition of 0.3 mg of solid TSTU, the resulting mixture is incubated at room temperature for 10 min. NIMS analysis shows clearly the desired product formation. This assay method for detecting carboxylic acid has features like mild reaction condition, compatible with aqueous solution and can be miniaturized to save reagents and solvents and is easy to operate as well.

Figure 13:
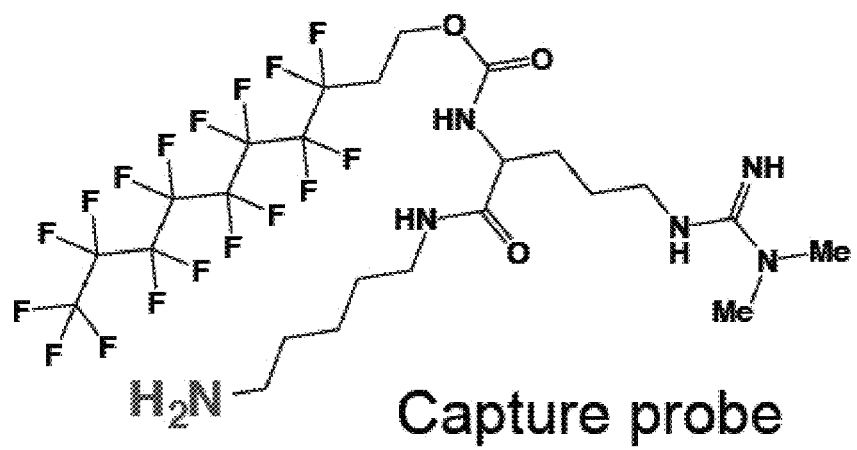
FIG. 13 shows an exemplary capture probe and capture of acetic acid.
Figure 13:
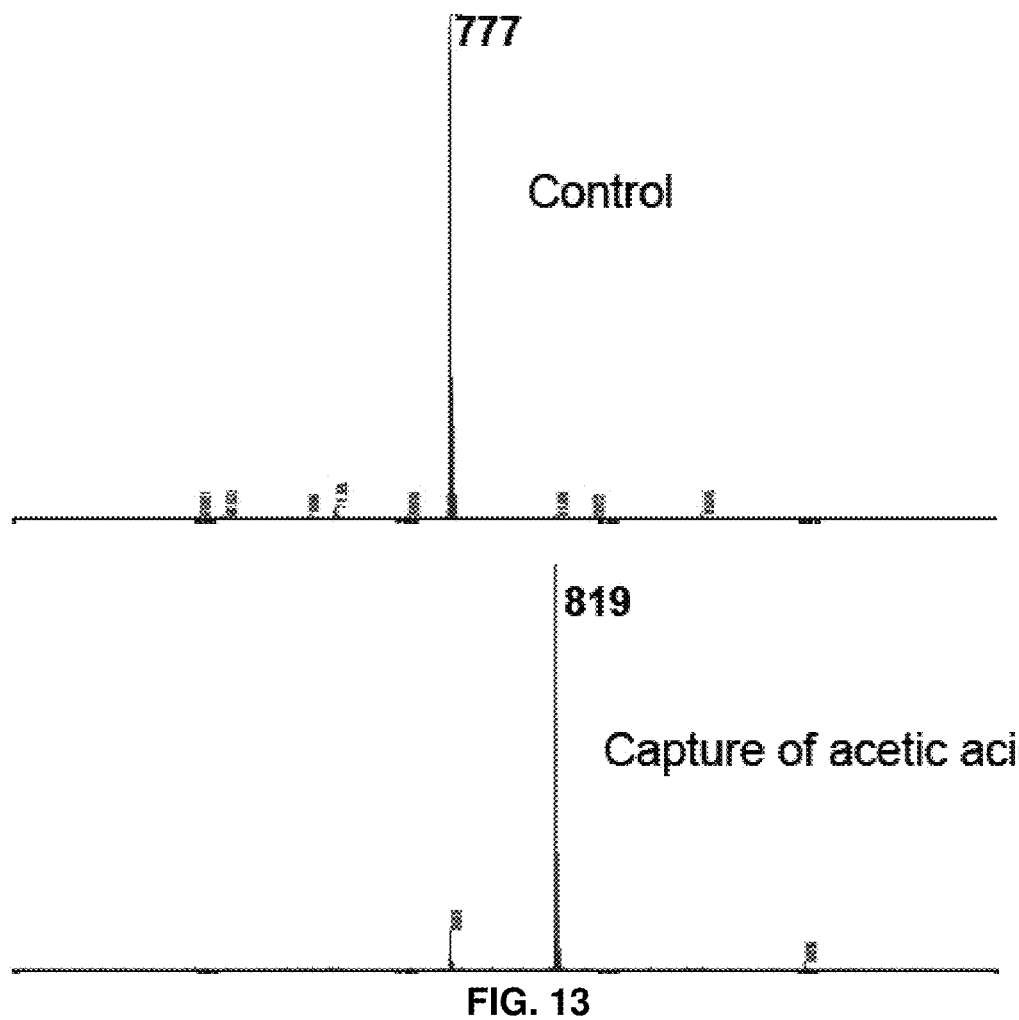
Figure 14:
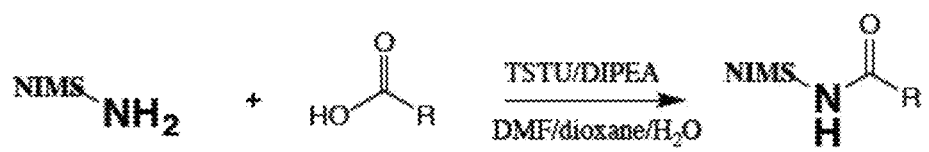
FIG. 14 shows TSTU and an amide bond formation in the capture of a carboxylic acid by the capture probe.
Figure 14:
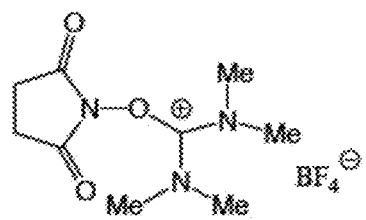

FIGS. 13 and 14 provide probes for the capture of carboxylic acid. The assay protocol comprises: 1) The capture probe is dissolved in a mixture of DMF/dioxane/H2O=2:2:1, use 10 μL of this solution; 2) 1 μL of DIPEA was added followed by 1 uL of HOAc.; 3) 0.3 mg TSTU was added; 4) Incubated at room temperature for 10 mins; and 5) NIMS analysis.

Development of Amine Active Probe to Study Peptide and Proteins 10 mg of the amine-reactive probe is dissolved in 100 μL of phosphate buffer (pH7.2, 50 mM) to make a 0.1 M stock solution. To 10 μL of above solution in an Eppendorf vial is added a 1 μL of lysine (50 mM in D.I. water). The resulting mixture is incubated at room temperature for 30 mins. NIMS analysis shows desired product formation. This new assay methods for capture peptides/proteins has features like mild reaction conditions at room temperature, compatible with aqueous solutions and can be miniaturized to save reagents.

Figure 15:
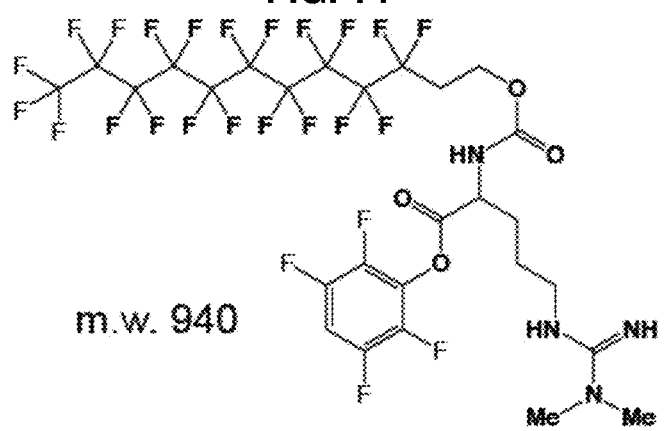
FIG. 15 shows an TFP ester, an exemplary probe for the primary amine and capture of a primary amine.
Figure 15:
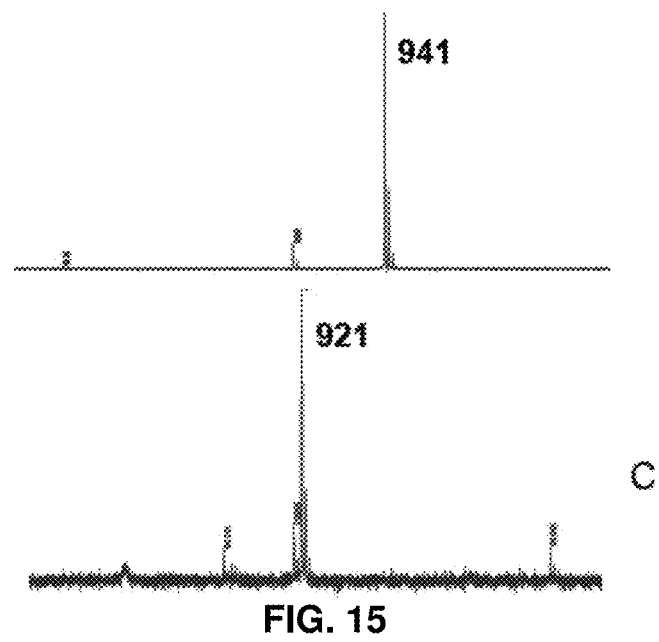
Figure 16:
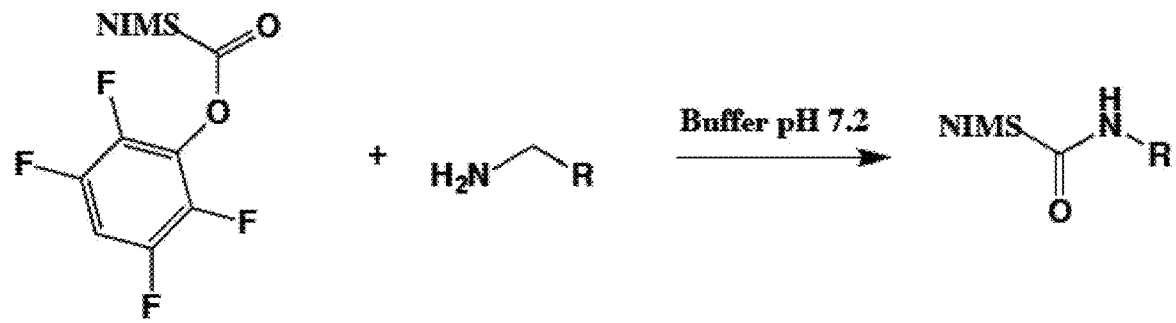
FIG. 16 shows the reaction of the TFP ester capturing a primary amine.
Figure 17:
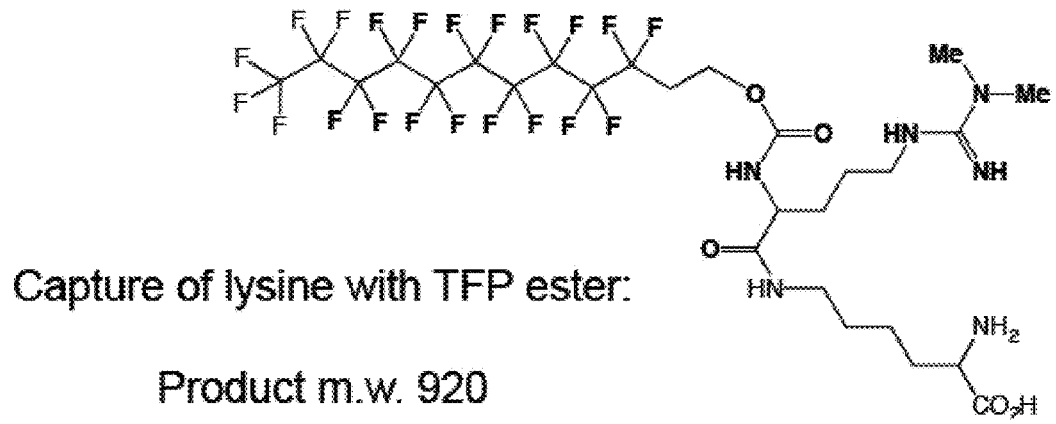
FIG. 17 shows an TFP ester with a captured lysine.

FIGS. 15-17 provide probes for the detection of peptides/proteins. The assay protocol comprises: 1) TFP ester is dissolved in phosphate buffer pH 7.2; 2) Primary amine is added; 3) Incubated at room temperature for 30 mins; and 4) NIMS analysis. The features of this protocol is that it is mild, the reactions take place in an aqueous condition, and the protocol is easy to operate.

Method to Detect Alcohols by NIMS

Oxidation under mild aqueous condition: A solution of alcohol (e.g. 1-dodecanol 18.6 mg), TEMPO (1.6 mg) and TBACl (2.8 mg) in a mixture of dichloromethane (1 mL) and 1 mL of an aqueous solution of NaHCO$_3$ (0.5 M) and K$_2$CO$_3$ (0.05 M) are stirred at room temperature. Then 20 mg of N-Chlorosuccinimide is added and the resulting mixture is stirred at room temperature for 12 h. Transfer 2 μL of sample in above dichloromethane layer to 6 μL or pH 1.3 glycine buffer (100 mM). Then 3 μL of a mixture of acetonitrile and methanol (v/v=2:1) is added, followed by the addition of internal standard and aminoxy-alkyl probe. The resulting mixture is incubated at room temperature for 12 h and NIMS analysis quantify the oxime-adduct of the aldehydes derived from the alcohol oxidation.

Figure 18:
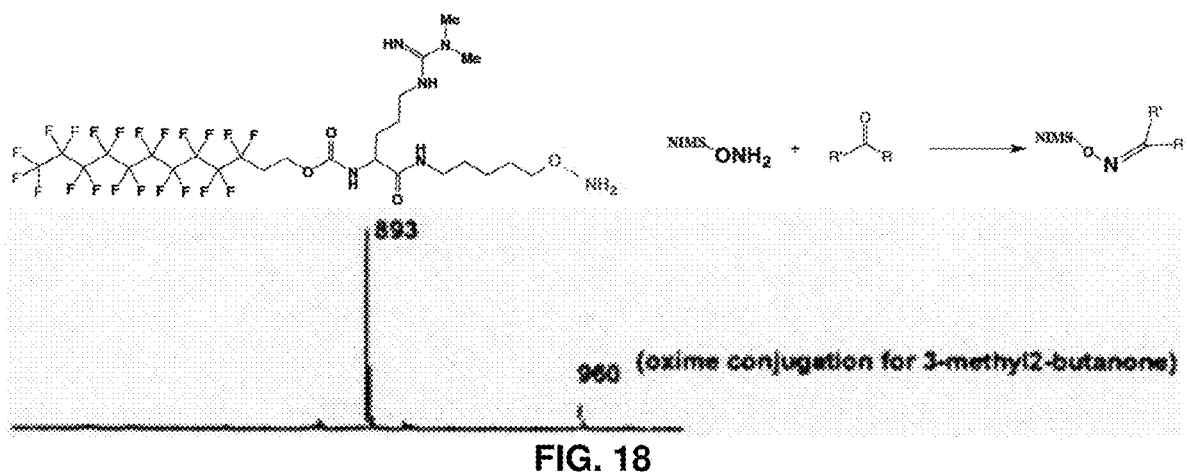
FIG. 18 shows a probe for ketone detection and the reaction for the capture of the ketone.

FIG. 18 provides probes for the detection of ketones. This probe has a higher molecular weight in order to avoid the problematic low molecular mass region for ketone detection.

Figure 19:
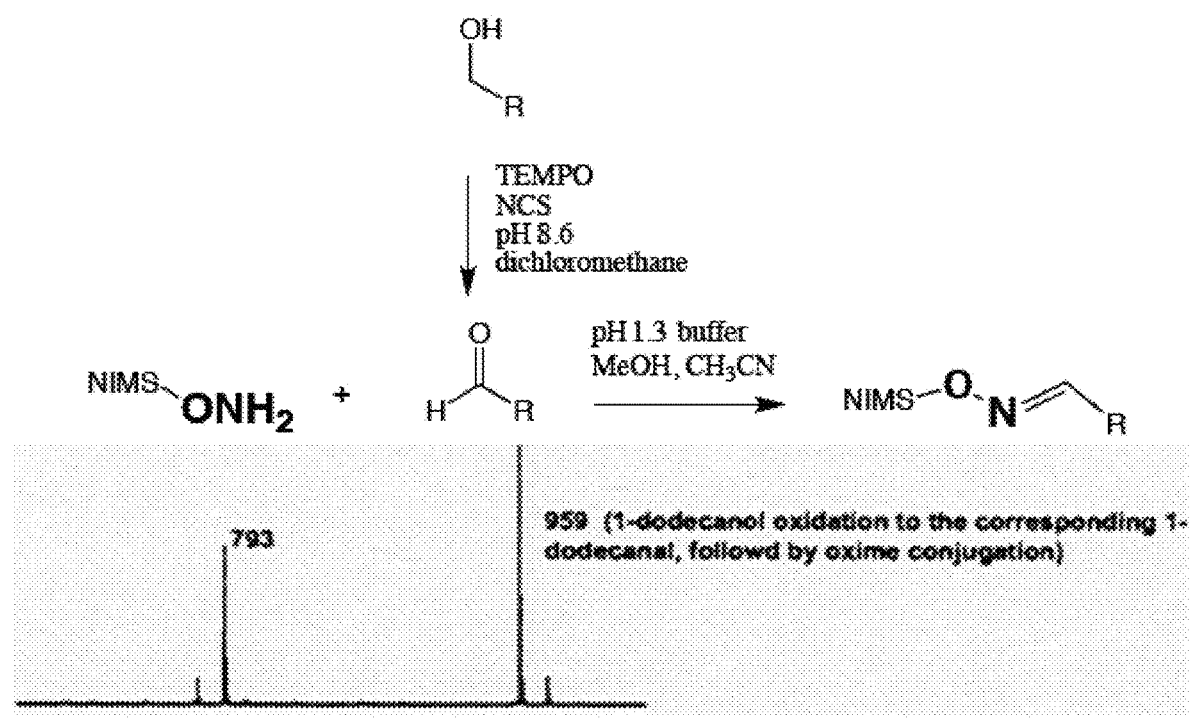
FIG. 19 shows the oxidation of an alcohol into ketone and the reaction for the capture of the ketone.

FIG. 19 provides a scheme for detecting alcohol by first converting it into a ketone and then detecting the ketone. Alcohol is first oxidized to the corresponding ketone under mild reaction conditions and the ketone is captured by the oxime-NIMS probe for quantitation.

Shown herein are chemical probes developed for the investigation of ligninases (enzymes responsible for the deconstruction of lignin): to capture compounds with primary amines (peptides, proteins) and to detect biofuels products (carboxylic acid, ketones, alcohols). Especially, these assay methods can be easily extended to use the high throughput platforms that have been built for screening cellulases and hemicellulases to significantly increase the throughput. In conclusion, these tools enable rapid discovery of high performance enzymes and cocktails, and biofuels strains with high titre products, and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for analysis of enzyme activity in a sample, comprising:
providing NIMS substrates incorporating one or more of, or simulating H, G, or S lignin units linked by one or more, beta-O-4, 5-5' (biphenyl), β-5 (phenylcoumaran), β-β, and 4-O-5 (diaryl ether) linkages, and tagging each substrate of the NIMS substrates designed with a unique mass fluorous tag or perfluoronated affinity moiety;
performing ligninase oxidation reactions on the tagged NIMS substrates designed to generate tagged reaction products using one or more enzymes in the sample; and
identifying and analyzing the tagged reaction products of the ligninase oxidation reactions by nanostructure-initiator mass spectrometry (NIMS).

2. The method of claim 1, wherein identifying and analyzing the reaction product of the ligninase oxidation reactions by NIMS comprises applying the reaction products to a hydrophobic NIMS chip surface, wherein the tagged reaction products interact with the NIMS chip surface via fluorous-phase-interactions.

3. The method of claim 1, wherein the method further comprising: performing kinetics study and quantification of ratios of products to substrates of the ligninase oxidation reactions to determine the enzyme activity in the sample.

4. The method of claim 1, wherein the providing step comprises designing the NIMS substrates.

5. The method of claim 1, the providing step comprises providing a NIMS substrate incorporating, or simulating H, G, or S lignin units linked by, a beta-O-4 linkage.

6. The method of claim 5, wherein the NIMS substrate is Compound A.

7. The method of claim 6, wherein the NIMS substrate is Compound A-1a or A-1b.

8. The method of claim 1, the providing step comprises providing a NIMS substrate incorporating, or simulating H, G, or S lignin units linked by, a 5-5' (biphenyl) linkage.

9. The method of claim 8, wherein the NIMS substrate is Compound B.

10. The method of claim 9, wherein the NIMS substrate is Compound B-1a or B-1b.

11. The method of claim 1, the providing step comprises providing a NIMS substrate incorporating, or simulating H, G, or S lignin units linked by, a $\beta$-5 (phenylcoumaran) linkage.

12. The method of claim 11, wherein the NIMS substrate is Compound C.

13. The method of claim 12, wherein the NIMS substrate is Compound C-1a or C-1b.

14. The method of claim 1, the providing step comprises providing a NIMS substrate incorporating, or simulating H, G, or S lignin units linked by, a $\beta$-$\beta$ linkage.

15. The method of claim 14, wherein the NIMS substrate is Compound D.

16. The method of claim 15, wherein the NIMS substrate is Compound D-1a or D-1b.

17. The method of claim 1, the providing step comprises providing a NIMS substrate incorporating, or simulating H, G, or S lignin units linked by, a 4-O-5 (diaryl ether) linkage.

18. The method of claim 17, wherein the NIMS substrate is Compound E.

19. The method of claim 18, wherein the NIMS substrate is Compound E-1a or E-1b.

20. The method of claim 1, wherein the mass fluorous tag or perfluoronated affinity moiety is Compound 1a or 1b.

21. The method of claim 1, wherein the providing step comprises providing a mixture of NIM substrates comprising (1) a NIMS substrate incorporating, or simulating H, G, or S lignin units linked by, a beta-O-4 linkage; (2) a NIMS substrate incorporating, or simulating H, G, or S lignin units linked by, a 5-5' (biphenyl) linkage; (3) a NIMS substrate incorporating, or simulating H, G, or S lignin units linked by, a $\beta$-5 (phenylcoumaran) linkage; (4) a NIMS substrate incorporating, or simulating H, G, or S lignin units linked by, a $\beta$-$\beta$ linkage; and, (5) a NIMS substrate incorporating, or simulating H, G, or S lignin units linked by, a 4-O-5 (diaryl ether) linkage.

22. The method of claim 21, wherein the mixture of NIMS substrates comprises Compound A, Compound B, Compound C, Compound D, and Compound E.

23. The method of claim 22, wherein the mixture of NIMS substrates comprises Compound A-1a or A-1b, Compound B-1a or B-1b, Compound C-1a or C-1b, Compound D-1a or D-1b, and Compound E-1a or E-1b.

* * * * *